United States Patent [19]
Banerian

[11] Patent Number: 5,769,222
[45] Date of Patent: Jun. 23, 1998

[54] ANGIOGRAPHY GUIDE WIRE CONTAINER

[76] Inventor: Kirk Banerian, 7105 Glenburnie, Clarkston, Mich. 48346

[21] Appl. No.: 819,502

[22] Filed: Mar. 17, 1997

Related U.S. Application Data

[63] Continuation-in-part of Ser. No. 470,937, Jun. 6, 1995, Pat. No. 5,611,428.

[51] Int. Cl.$^6$ .............................. B65D 83/10; A61B 5/00
[52] U.S. Cl. .......................... 206/364; 128/772; 206/210; 206/438; 604/171
[58] Field of Search .................................... 206/363, 364, 206/438, 409, 210; 604/171, 265; 128/772

[56] References Cited

U.S. PATENT DOCUMENTS

| | | | |
|---|---|---|---|
| 3,100,487 | 8/1963 | Bathish | 206/364 X |
| 3,683,928 | 8/1972 | Kuntz | 206/364 X |
| 3,854,479 | 12/1974 | Duke | 206/364 X |
| 4,607,746 | 8/1986 | Stinette . | |
| 4,721,123 | 1/1988 | Cosentino et al. | 604/171 X |
| 4,754,877 | 7/1988 | Johansson et al. | 206/364 |
| 4,886,500 | 12/1989 | Lazarus et al. . | |
| 4,936,448 | 6/1990 | Holloway | 206/364 |
| 5,125,416 | 6/1992 | Phillips | 206/409 X |
| 5,135,516 | 8/1992 | Sahatjian et al. . | |
| 5,242,428 | 9/1993 | Palestrant . | |
| 5,290,242 | 3/1994 | Vaillancourt . | |
| 5,310,524 | 5/1994 | Campbell et al. . | |
| 5,611,428 | 3/1997 | Banerian | 206/364 |

Primary Examiner—Bryon P. Gehman
Attorney, Agent, or Firm—Gifford, Krass, Groh, Sprinkle, Patmore, Anderson & Citkowski, P.C.

[57] ABSTRACT

There is disclosed herein a container for use in storing, cleansing, and moistening a guide wire or other flexible, elongated medical device between uses during medical procedures. The container has a base having an upper surface and a lower surface. A continuous side wall extends upwardly from the base forming a basin for retaining a coiled, flexible medical device such as a guide wire. A retaining flange is attached to the side wall and extends across at least a portion of the base to retain the free ends of the guide wire in the basin. A guide arm is attached to the side wall, and extends across at least a portion of the base so that the guide arm guides the coiled medical device onto the upper surface of the base as the medical device is inserted. The container may also have a plurality of ribs to keep the coiled guide wire from touching the base of the container. A channel or retention clips may be positioned on the lower surface of the base for retaining the guide wire in a fixed position so that the guide wire does not contact itself during packaging, sterilization and storage.

21 Claims, 7 Drawing Sheets

_Fig-3_

_Fig-4_

_Fig-5_

_Fig-6_

ANGIOGRAPHY GUIDE WIRE CONTAINER

CROSS-REFERENCE TO RELATED APPLICATIONS

This application is a continuation in part of U.S. patent application Ser. No. 08/470,937 filed Jun. 6, 1995, now U.S. Pat. No. 5,611,428.

BACKGROUND OF THE INVENTION

I. Field of the Invention

The present invention relates generally to containers and, more particularly, to a container for holding angiography guide wires, or other elongated, flexible medical devices, in between uses during medical procedures.

II. Description of the Prior Art

Certain medical procedures involve the insertion of a catheter into the human body, injecting a contrast material through the catheter, and then obtaining images of those portions of the body. In this fashion, various abnormalities that are in the body can be detected.

In order to insert a catheter into the appropriate portions of the body, a guide wire for the catheter must first be inserted. Initially, a needle is used to enter the body. A guide wire is then inserted through the needle into the body, after which the needle is removed. A catheter is then inserted over the guide wire, the guide wire thereby "guiding" the catheter into the appropriate position. Once the catheter is in place, the guide wire is then removed so that the contrast material can be injected though the catheter. Problems arise in finding a means for containing the guide wire between uses during each procedure.

At the present time, the handling of guide wires outside of the catheter during angiography is both awkward and inefficient. During angiography, the angiographer must insert the guide wire through the needle hub to gain catheter access, as well as insert and remove the guide wire for each artery selectively catheterized. Additionally, if a guide wire remains in a catheter for prolonged periods of time (i.e., in excess of two minutes) there is danger of embolic sequelae. As a result, the angiographer must remove the guide wire, flush clean the catheter, and thereafter reinsert the guide wire. This requires even additional handling of the guide wire when difficult arteries need to be accessed. A guide wire is typically inserted and removed from a patient about a half dozen times during a four vessel cerebral angiogram. For more complex cases such as spinal angiograms, a guide wire may be inserted and removed from the patient a dozen times or more.

Each time the guide wire is removed from the patient, it is wiped clean of the adherent blood, coiled to a more manageable size, and stored either by wrapping the loose end of the guide wire around the coil, or placing a weighted object on the coiled guide wire to prevent it from uncoiling or "springing open." Each time the guide wire is removed from the catheter, it comes in contact with air, allowing residual adherent blood to dry, harden, and form a potential embolic nidus. Furthermore, even though a guide wire may be carefully wiped, a certain amount of residual blood will always remain on the surface of the guide wire. An additional problem is that the unstable guide wire can become contaminated by falling onto the floor or coming into contact with an unclean surface in between uses. When this happens, the contaminated guide wire must be discarded, and replaced by a sterile guide wire.

A further problem with the present system is that after each time the guide wire is removed from the catheter, an angiographer must use both hands to close the catheter valve so as to prevent the backflow of blood from the catheter. Since both hands must be used to close the catheter valve, it is exceedingly difficult for one person to also wipe, coil, and find a suitable resting spot for the guide wire. When the guide wire is next needed, it must be carefully retrieved and unwrapped, o that it does not "spring open." When using a guide wire with a hydrophilic coating, (particularly useful for reaching difficult and tortuous arteries), there is an additional step of moistening the guide wire which must be done prior to each insertion.

SUMMARY OF THE PRESENT INVENTION

The present invention provides a device which overcomes all of the above-mentioned disadvantages of the previously-known methods of storing, cleaning, and moistening the guide wires during angiographic procedures.

In brief, the present invention comprises a container for use in angiographic procedures or other medical procedures such as endoscopic procedures utilizing an elongated, flexible medical device. The container comprises a base, and side walls which extend upwardly and inwardly from the base. The container is open at the top so that a coiled guide wire can be placed inside the container. The cross-sectional area of the opening is smaller than the cross-sectional area of the base, and the opening and the base may be of complementary shape.

The invention further comprises a plurality of standoff members extending from the sides and/or base of the container in order to suspend the coiled guide wire in a bathing solution that may be disposed inside the container. At least one finger slot aids in the removal of the coiled guide wire from the container during the angiographic procedure. The guide wire container can be attached to any area around a patient where it is most needed.

An alternate embodiment of the present invention includes a base encircled by a continuous side wall to form a basin. Retaining flanges and guide arms guide the coiled guide wire into the basin and retain it in the proper position.

BRIEF DESCRIPTION OF THE DRAWINGS

A better understanding of the present invention will be had upon reference to the following detailed description, when read in conjunction with the accompanying drawings, wherein like referenced numerals refer to parts throughout the several views, and in which.

DETAILED DESCRIPTION OF A PREFERRED EMBODIMENT OF THE PRESENT INVENTION

With reference first to FIGS. 1–5, perspective, plan and cross-sectional views of the container 10 of the present invention is there shown. The container 10 has a base 12, and side walls 14 which extend upwardly and inwardly from the base 12. The upper edges 16 of the side walls 14 form an opening 18 in the container 10 through which the coiled guide wire 20 can be inserted and removed. The cross-sectional area of the opening 18 is smaller than the cross-sectional area of the base 12. Both the opening 18 and the base 12 may be of a complementary shape. Once placed through the opening 18, the potential energy in a coiled guide wire 20 will drive the guide wire 20 toward the base 12 of the container 10.

Figure 1:
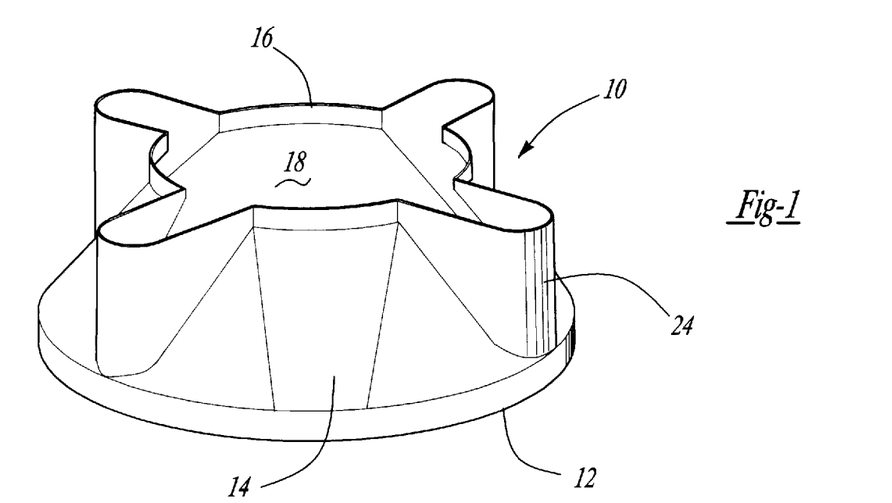
FIG. 1 is a perspective view of the container of the present invention.
Figure 2:
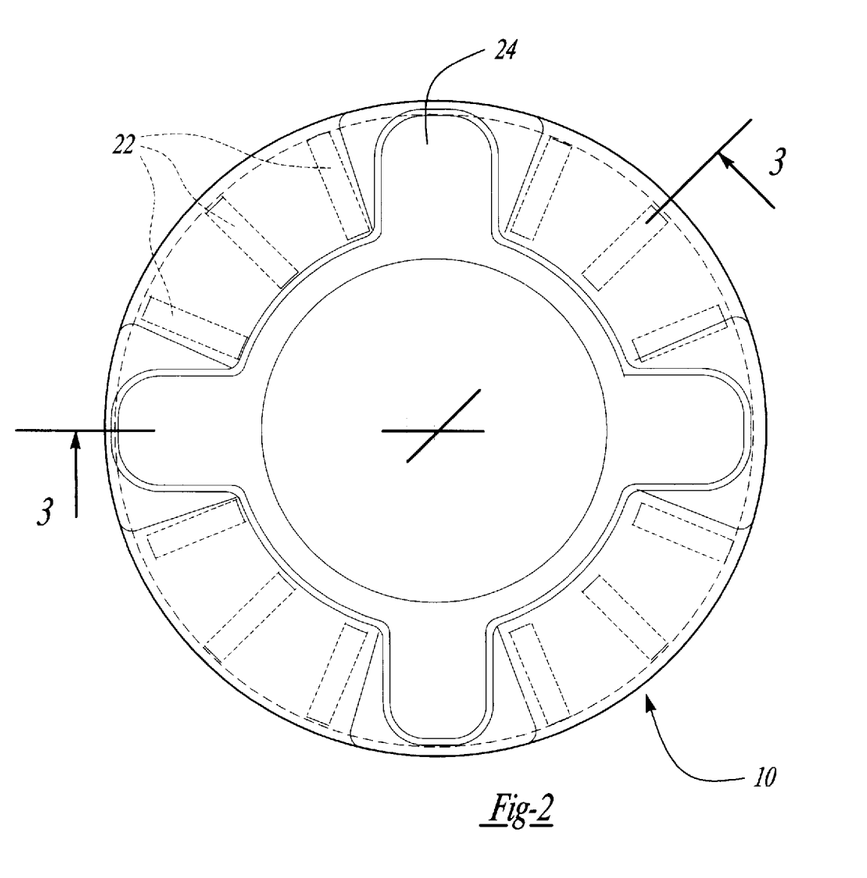
FIG. 2 is a plan view of the container of the present invention.
Figure 3:
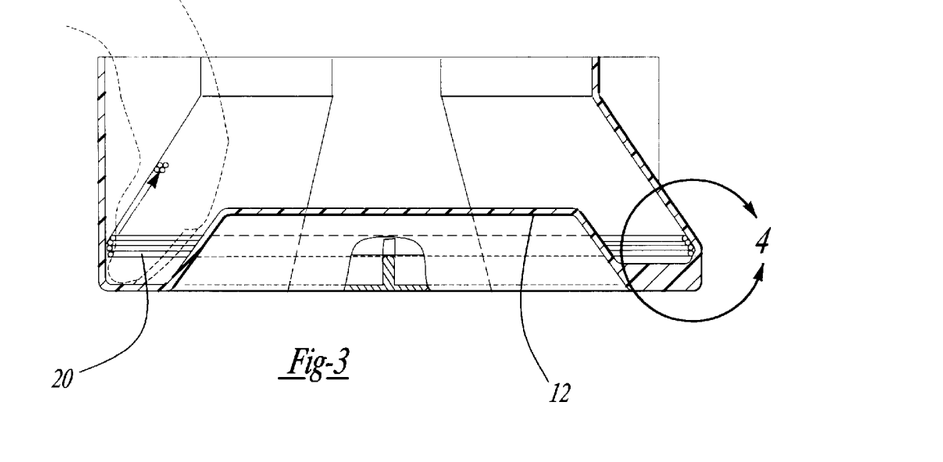
FIG. 3 is a cross-sectional view of the container of the present invention, taken along lines 3—3 of FIG. 2.
Figure 4:
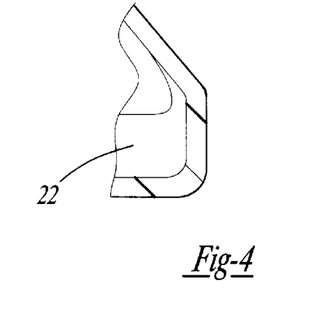
FIG. 4 is an enlarged view of circle 4, taken from FIG. 3, showing a stand-off member.
Figure 5:
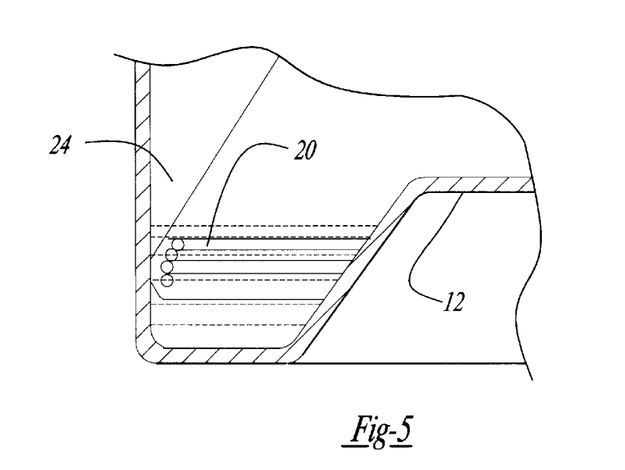
FIG. 5 is an enlarged view of a guide wire suspended in the container of the present invention.

In one preferred embodiment of the invention, a plurality of standoff members 22 extend upwardly from the inner surface of the base 12. The standoff members 22 can also extend inwardly from the inner surface of the side walls 14. The standoff members 22 help to keep the coiled guide wire 20 suspended away from the base 12 and sides 14 of the container 10.

The container 10 of the present invention can also have one or more finger slots 24 extending outwardly from the opening 18 of the container 10 to a point at or near the base 12 of the container 10. The purpose of these finger slots 24 or protrusions is to allow easy removal of the coiled guide wire 20 through the container opening 18.

In another preferred embodiment of the present invention, the center portion of base 12 is elevated above the outer area of the base 12, as best shown in FIG. 3. Therefore, when a bathing solution is added to the container 10 to moisten and cleanse the coiled guide wire 20 stored within, the bathing solution will pool toward the outer edges of the container 10, where the coiled guide wire 20 is resting. This feature helps to conserve the bathing solution, because less is required to moisten and cleanse the coiled guide wire 20.

Figure 6:
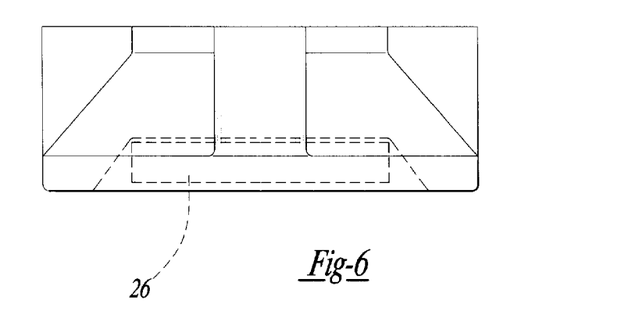
FIG. 6 is a cross-sectional view showing the optional vibrating means.

As shown in FIG. 6, the container 10 may also have vibrating means 26 attached to it, thereby transforming the container 10 into a type of ultrasonic cleaning container. That is, the vibrator 26 would vibrate the solution within the container 10, thus assuring that every portion of the coiled guide wire 20 is moistened and cleansed in between uses during the angiographic procedure. The container 10 of the present invention can be made from injection molded plastic, metal, or any other material as is known in the art.

In a preferred embodiment, the container 10 further has attachment means (not shown) such as double sided tape, clips, or other means of attachment, as is known in the art, so that the container 10 can be easily attached and secured to an area around a patient. This would insure that the coiled guide wire 20 within the container 10 remains nearby in between uses during the angiographic procedure, and would prevent the container 10 from tipping over or falling onto the floor, thereby minimizing contamination.

Figures 7, 8:
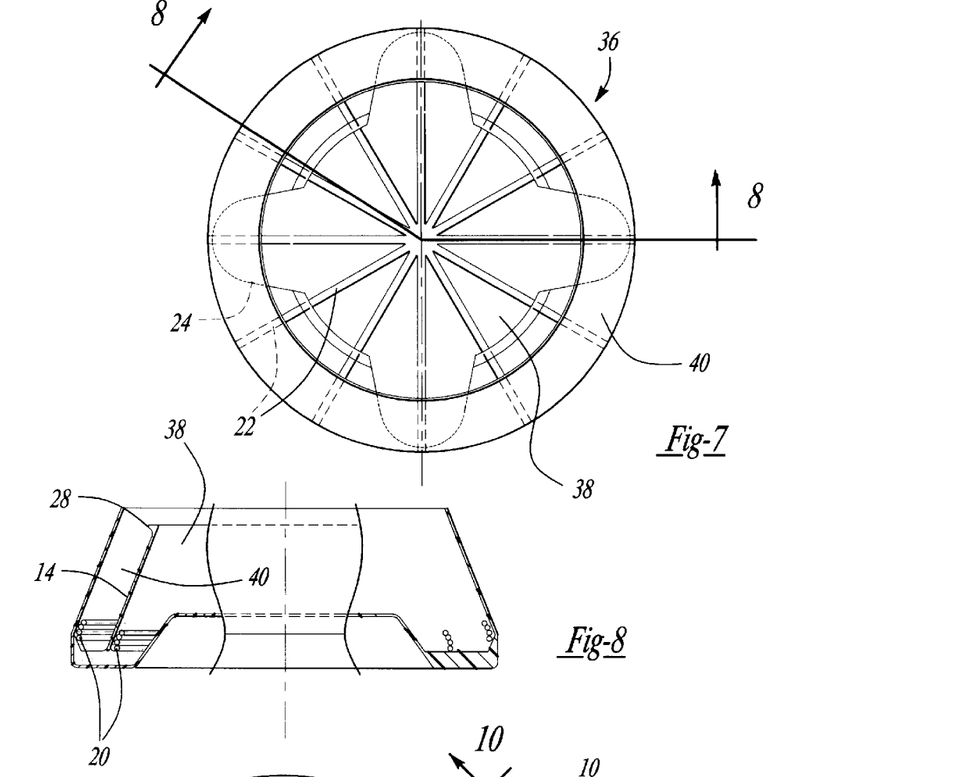
FIG. 7 is a plan view of an alternate embodiment of the container of the present invention showing nested container chambers.
FIG. 8 is a cross-sectional view of nested containers, taken along lines 8—8 of FIG. 7.

As best shown in FIGS. 7 & 8, in another embodiment of the present invention, a plurality of containment chambers 36 can be provided, each nested inside the other. The inner nested chambers 38 may have either continuous or non-continuous side wall portions 14. In order to insure that a coiled guide wire 20 is properly disposed within the proper chamber 36, an inner nested chamber 38 can have an outwardly extending lip portion 28, over which the coiled guide wire 20 can be hung, and then dropped into the next outer-most nested chamber 40. This embodiment allows for the simultaneous storing and cleansing of multiple guide wires 20. By nesting the chambers 36, the various guide wires 20 can be maintained separately.

Figure 9:
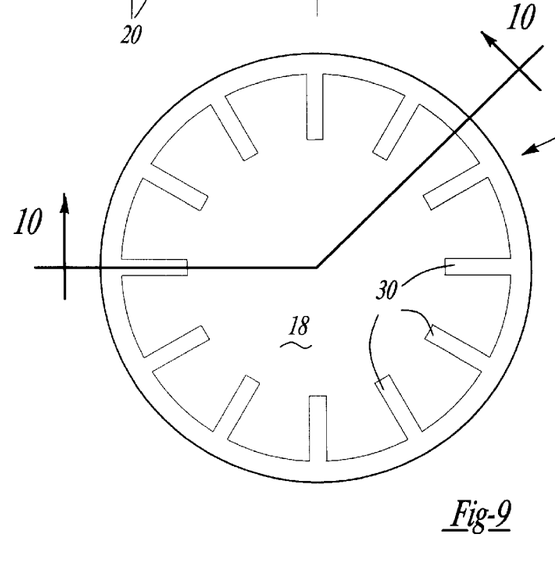
FIG. 9 is a plan view of an alternate embodiment of the container of the present invention showing guide rails.
Figure 10:
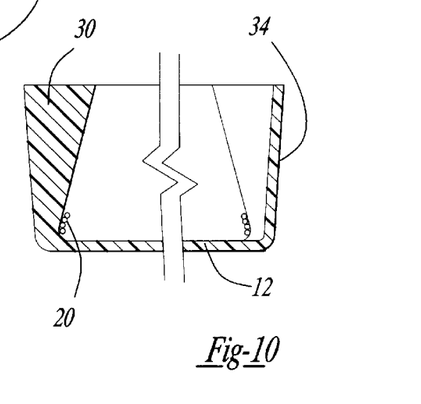
FIG. 10 is a cross-sectional view taken along lines 10—10 of FIG. 9.

As best shown in FIGS. 9 & 10, in another embodiment of the present invention, a plurality of guide rails 30 extend upwardly and inwardly from the base 12 of the container 10. The upper edges (not shown) of the guide rails 30 form an opening 18 into which the coiled guide wire 20 is placed. Once released, the potential energy in the coiled wire 20 will drive it into the base 12 of the container 10, as has already been described. The side walls 34 surround the guide rails 30 in order to contain a bathing solution disposed within. In this embodiment, the side walls 34 are not necessary to contain the coiled guide wire 20.

FIGS. 11–16 show an alternate embodiment of the invention wherein container 110 includes a base 112 having an upper surface 114. Although the upper surface 114 is depicted as a substantially flat surface, the upper surface 114 may be configured to minimize the amount of bathing solution required to moisten and cleanse the coiled guide wire 126. Additionally, a groove may be provided in upper surface 114 to enable a user to more easily grasp and remove the guide wire 126. A continuous side wall 122 encircles base 112 to form a basin 124 which is suitable for retaining a coiled guide wire 126 having two free ends 125 and 127. Preferably, the base 112 is elongated with an insertion end 118 and a preferred removal end 120.

Figures 11, 12, 13:
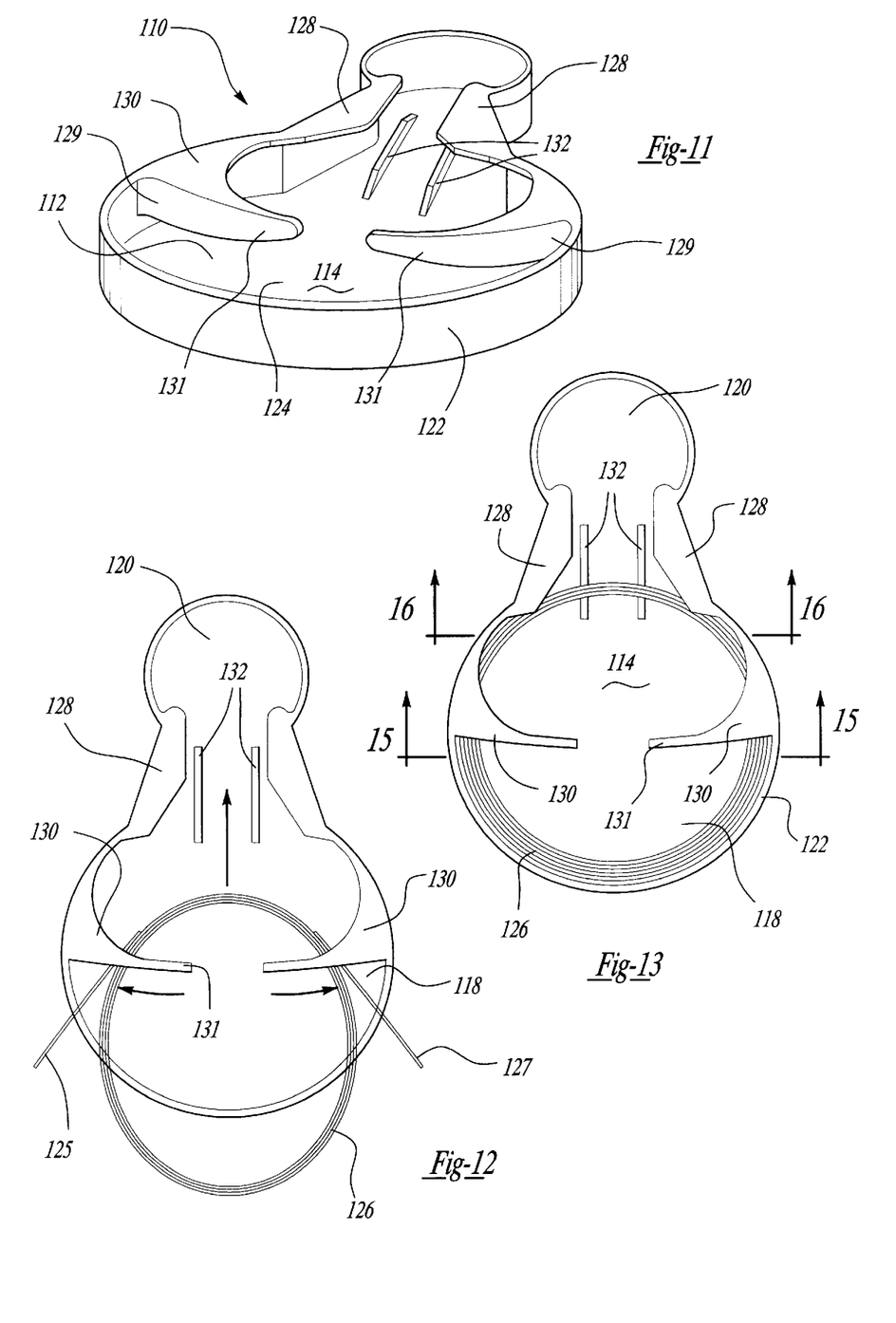
FIG. 11 is a perspective view of an alternate embodiment of the container of the present invention.
FIG. 12 is a plan view of the container depicted in FIG. 11 during insertion of a guide wire.
FIG. 13 is a plan view of the container depicted in FIG. 11 having a guide wire inserted therein.

As shown in the preferred embodiment in FIGS. 11, 12 and 13, at least one guide arm 130 is provided which extends inwardly from side wall 122 and is spaced apart from the upper surface 114 of the base 112. Preferably, the end 129 of guide arm 130 lies lower than the end 131 to provide lead-in for the guide wire 126.

Figure 21:
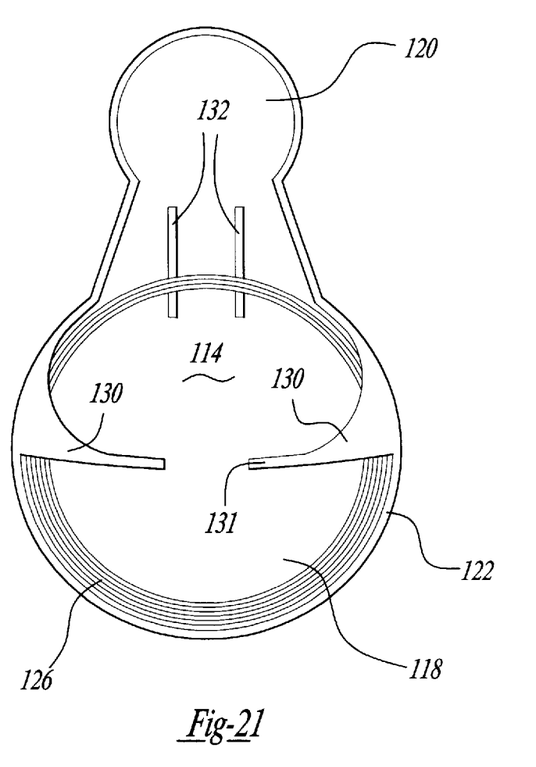
FIG. 21 is a plan view of an alternate embodiment of the container.

As shown in FIGS. 11–13, retaining flanges 128 are preferably mounted on the upper portion of side wall 124 and extend toward each other to retain the coiled guide wire 126 in the basin 124. At least one retaining flange 128 should be used in the present invention, although two retaining flanges are preferable. As depicted in FIG. 21, a container need not include a retaining flange 128 to properly retain, cleanse and moisten guide wire 126.

Figure 15:
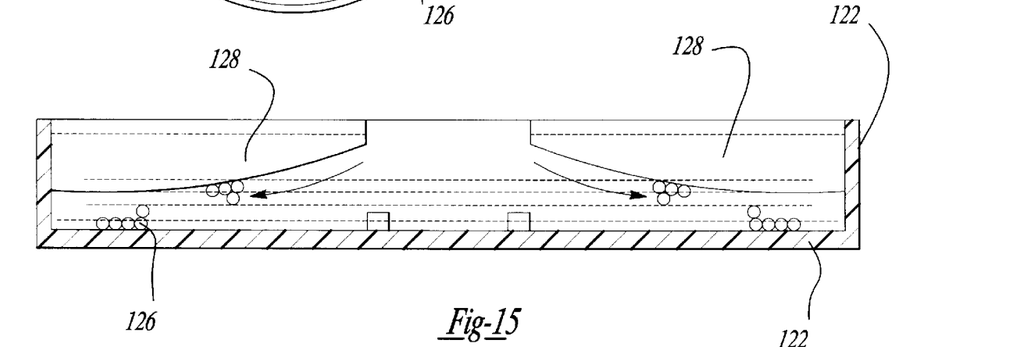
FIG. 15 is a cross-sectional view of the embodiment depicted in FIG. 13 taken along line 15—15.

As shown in FIG. 12, the coiled guide wire 126 is inserted into the insertion end 118 of container 110 and drawn under guide arms 130. As shown in FIG. 15, the ends 131 of guide arms 130 provide a lead-in for guide wire 126. As the coiled guide wire is drawn beneath the guide arms, the guide wire moves toward a position proximate to the side wall 122.

Figure 16:
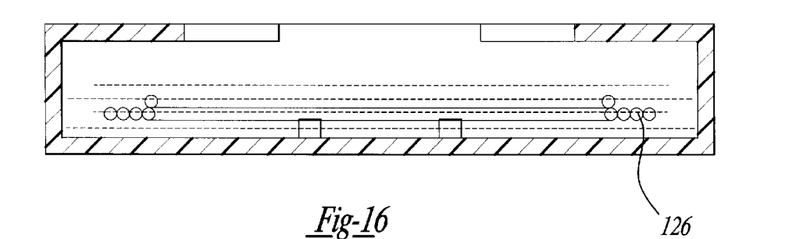
FIG. 16 is a cross-sectional view of the embodiment depicted in FIG. 13 taken along line 16—16.

During the insertion of the guide wire into the container as shown in FIG. 13, the guide wire may be drawn slightly under flanges 128 so that the free ends 125 and 127 of the coiled guide wire are retained in basin 124 by retaining flanges 128 and guide arms 130. FIG. 16 shows a cross-sectional view the guide wire 126 within the basin 124.

Figure 14:
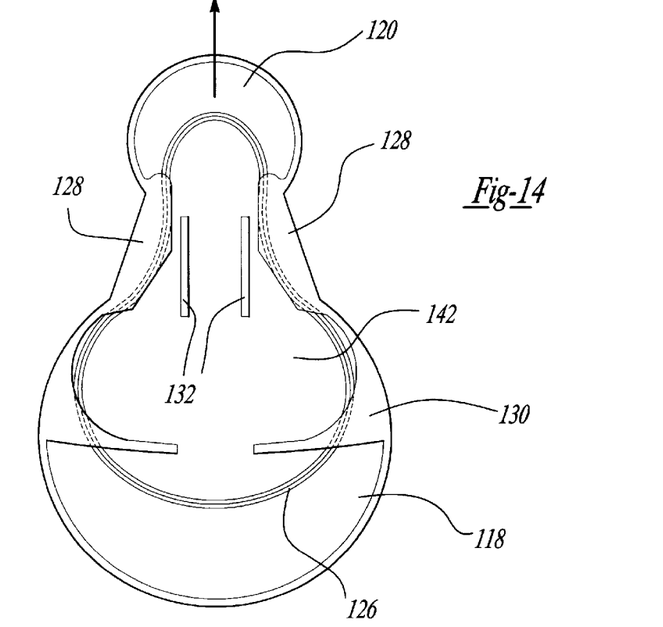
FIG. 14 is a plan view of the container depicted in FIG. 13 showing the preferred method of removal of the guide wire.

As shown in FIG. 14, guide wire 126 is removed by grasping a portion of exposed coil and drawing it through removal end 120. Alternately, the guide wire 126 may be removed from container 110 by grasping the guide wire between flanges 128 and drawing the guide wire out through the central portion 142 of the container. In addition, a free end 125 or 127 may be grasped and pulled from the container by the free end, uncoiling the guide wire as it is removed from the container. In a manner similar to that described above, bathing solution and/or vibrating means may be utilized in conjunction with this embodiment of the invention.

Figures 17, 18, 19, 20:
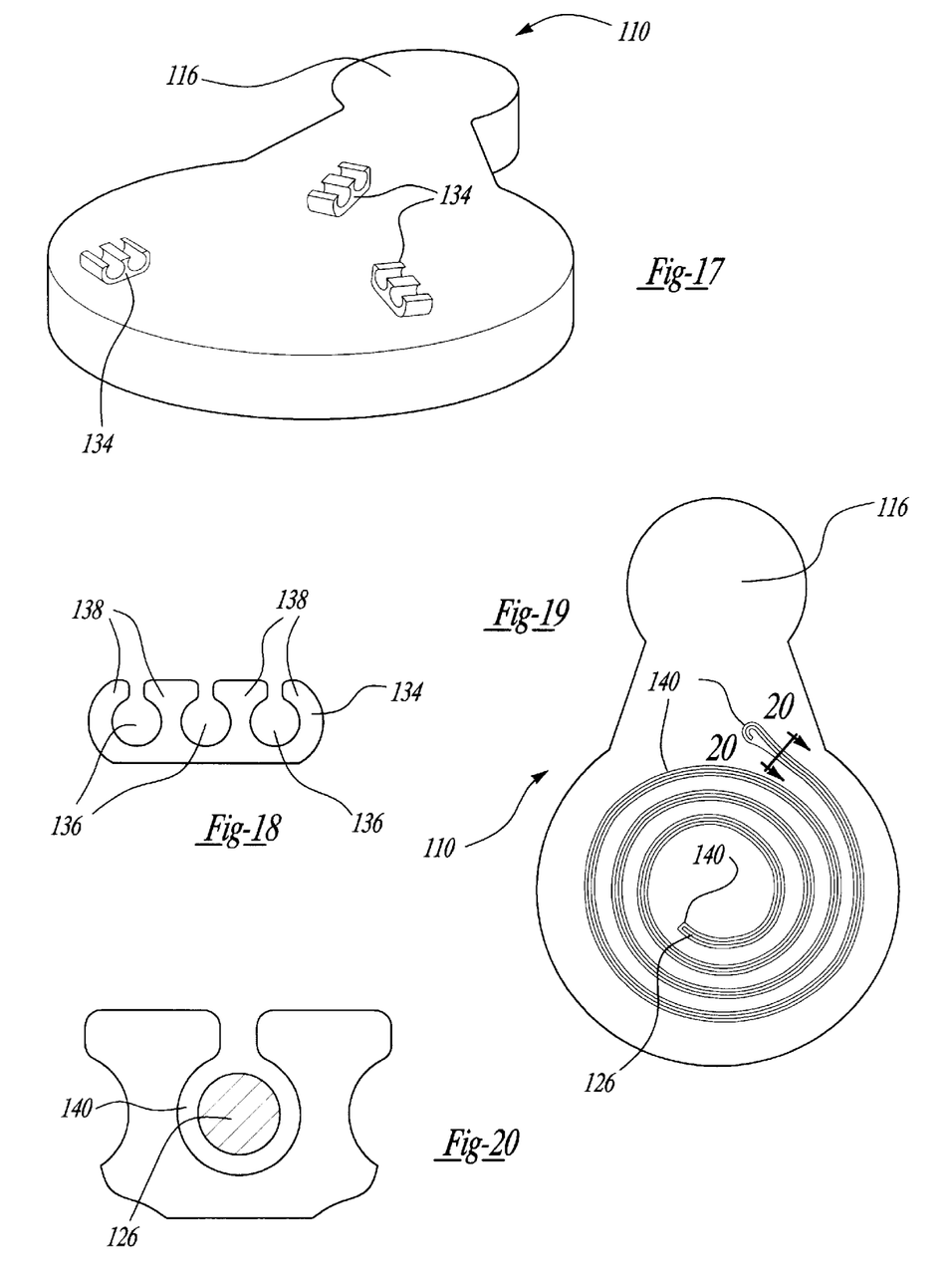
FIG. 17 is a perspective view of the lower surface of the container base.
FIG. 18 is a plan view of the clip depicted in FIG. 17.
FIG. 19 is a plan view of an alternate embodiment of the lower surface of the container base.
FIG. 20 is a partial cross-sectional view taken along line 20—20 in FIG. 19.

FIGS. 17–20 depict an alternate embodiment of the base 112 wherein a means for retaining the coiled guide wire 126 is attached to the lower surface 116. As shown in FIG. 17, a plurality of clips 134 are positioned on lower surface 116 in a circular arrangement. The clips 134, depicted in FIG. 18, are configured so that arms 138 may flex to permit guide wire 126 to be placed into and retained within openings 136. The guide wire 126 is retained in a coiled position so that the guide wire does not contact itself. The guide wire may be contained within a flexible tubing which is retained within clips 134. Preferably, the clips 134 are constructed of a flexible plastic.

FIG. 19 shows an alternate embodiment whereby a continuous channel 140 is provided in the lower surface 116 of base 112. The guide wire 126 is positioned within channel 140 so that the guide wire does not contact itself. In the preferred embodiment depicted in FIG. 20, the channel 140 is C-shaped. In an alternate embodiment, a retaining member (not shown) may be placed across a portion of the channels 140 to retain the guide wire in the channel. For example, a retaining member may be pivotably mounted to the lower surface 116 of base 112 so that, when the retaining member is pivoted to a position directly over the channel, the channel opening is blocked and the guide wire is retained within the channel. The retaining member may be pivoted to a position away from the channel 140 to permit the guide wire to be removed.

A sterilized guide wire may be retained on the lower surface 116 of base 112 for removal and use by the angiographer during a medical procedure. Guide wires may also be positioned on the lower surface 116 during a sterilization process. By retaining the guide wire in a position where the guide wire does not contact itself, hydrophilic guide wires may be attached to the lower surface 116 of base 112 during sterilization without damage to the guide wire.

The containers of the present invention can be used to store, cleanse and moisten guide wires between uses during angiography and for storage and sterilization. When the guide wire is removed from the patient, it is wiped to clean adherent blood, coiled, and dropped into the container 10 or drawn into container 110 where it settles to the bottom and is cleansed and moistened. When the guide wire is next needed, it is easily and quickly retrieved, premoistened. The present invention may improve embolic complications during angiography such as stroke, by cleaning the guide wire between uses. The containers of the present invention also reduces the time required to handle the guide wire, thereby minimizing angiography procedure time, important in reducing patient morbidity and mortality associated with the angiography procedure. This invention also contemplates use with catheters, as well as any elongated, flexible medical device requiring storage and/or cleansing.

Having described my invention, however, many modifications thereto will become apparent to those skilled in the art to which it pertains without deviation from the spirit of the invention as defined by the scope of the appended claims.

What is claimed is:

1. A container for use in medical procedures comprising:
    a base having an upper surface and a lower surface, the base defining an insertion end and an exposing removal end, each end allowing passage of an entire coiled flexible medical device having two free ends;
    a continuous side wall extending upwardly from and encircling the insertion and removal ends of the base forming a basin for retaining the coiled, flexible medical device;
    at least one retaining flange attached to the side wall and spaced apart from the upper surface of the base, the retaining flange extending across at least a portion of the base and configured to retain the free ends of the coiled medical device; and
    at least one guide arm attached to the side wall, each guide arm spaced apart from the upper surface of the base and extending across at least a portion of the insertion end of the base;
    whereby each guide arm guides the coiled medical device onto the upper surface of the base as the medical device is inserted at the insertion end, the retaining flange retaining the free ends of the coiled medical device during and after insertion into the basin.

2. The container of claim 1 further comprising a plurality of ribs positioned on the upper surface of the base.

3. The container of claim 1 further comprising a bathing solution contained within the basin.

4. The container of claim 3 further comprising means for vibrating the bathing solution within the basin.

5. The container of claim 1 further comprising means for retaining the flexible medical device in a coiled fashion on the lower surface of the base so that the coils of the medical device do not contact each other.

6. The container of claim 5 wherein the means for retaining the medical device includes a plurality of flexible clips.

7. The container of claim 5 wherein the means for retaining the medical device includes a continuous channel.

8. The container of claim 7 wherein the channel has a C-shaped cross-sectional area.

9. A container for use in medical procedures comprising:
    a base having an upper surface and a lower surface, the base defining an insertion end and an exposing removal end, each end allowing passage of an entire coiled flexible medical device having two free ends;
    a plurality of ribs positioned on the upper surface of the base;

a continuous side wall extending upwardly from and encircling the insertion and removal ends of the base forming a basin for retaining the coiled flexible medical device;

a pair of retaining flanges attached to the side wall, each retaining flange spaced apart from the upper surface of the base and extending across at least a portion of the base, the retaining flange configured to retain the free ends of the coiled medical device; and a pair of guide arms attached to the side wall, each guide arm spaced apart from the upper surface of the base and extending across at least a portion of the insertion end of the base;

whereby the guide arms guide the coiled medical device onto the upper surface of the base as the coiled medical device is inserted at the insertion end, the retaining flanges retaining the free ends of the coiled medical device during and after insertion into the basin.

10. The container of claim 9 further comprising means for retaining the flexible medical device in a coiled fashion on the lower surface of the base so that the coils of the medical device do not contact each other.

11. The container of claim 10 wherein the means for retaining the medical device includes a plurality of flexible clips.

12. The container of claim 10 wherein the means for retaining the medical device includes a continuous channel having an open end.

13. The container of claim 12 wherein the channel has a C-shaped cross-sectional area.

14. A container for use in medical procedures comprising:

an elongated base having an upper surface and a lower surface, the base defining an insertion end and an exposing removal end, each end allowing passage of an entire coiled flexible medical device having two free ends;

means for retaining an elongated, flexible medical device in a coiled fashion on the lower surface of the base;

a plurality of ribs positioned on the upper surface of the base;

a continuous side wall extending upwardly from and encircling the insertion and removal ends of the base forming a basin for retaining the coiled medical device;

a pair of retaining flanges attached to the side wall, each retaining flange spaced apart from the upper surface of the base and extending across at least a portion of the base, the retaining flange configured to retain the free ends of the coiled medical device; and a pair of guide arms attached to the side wall, each guide arm spaced apart from the upper surface of the base and extending across at least a portion of the insertion end of the base;

whereby the guide arms guide the coiled medical device onto the upper surface of the base as the medical device is inserted at the insertion end, the retaining flanges retaining the free ends of the coiled medical device during and after insertion into the basin.

15. The container of claim 14 wherein the means for retaining the medical device includes a plurality of flexible clips.

16. The container of claim 14 wherein the means for retaining the medical device includes a channel having an open end.

17. The container of claim 16 wherein the channel is C-shaped.

18. A method of containing an elongated, flexible medical device having two free ends in between medical procedures, said method comprising the steps of:

removing said medical device from a patient, coiling said medical device, disposing said medical device in a container, said container comprising a base having an upper surface and, a lower surface, the base defining an insertion end and an exposing removal end, each end allowing passage of an entire coiled flexible medical device having two free ends; a continuous side wall extending upwardly from and encircling the insertion and removal ends of the base forming a basin for retaining the medical device, at least one retaining flange attached to the side wall and spaced apart from the upper surface of the base, the retaining flange extending across at least a portion of the base and configured to retain the free ends of the coiled medical device, and at least one guide arm attached to the side wall, each guide arm spaced apart from the upper surface of the base and extending across at least a portion of the insertion end of the base.

19. The method of claim 18, further comprising the step of bathing said medical device in a bathing solution disposed within said container.

20. The method of claim 19, further comprising the step of vibrating said medical device within said bathing solution.

21. A container for use in angiographic procedures comprising:

a base having an upper surface and a lower surface, the base defining an insertion end and an exposing removal end, each end allowing passage of the entire coiled medical device having two free ends;

a continuous side wall extending upwardly from and encircling the insertion and removal ends of the base forming a basin for retaining the coiled, flexible medical device; and at least one guide arm attached to the side wall, each guide arm spaced apart from the upper surface of the base and extending across at least a portion of the insertion end of the base;

whereby each guide arm guides the coiled medical device onto the upper surface of the base as the medical device is inserted at the insertion end.

* * * * *

UNITED STATES PATENT AND TRADEMARK OFFICE
CERTIFICATE OF CORRECTION

PATENT NO. : 5,769,222
DATED : June 23, 1998
INVENTOR(S) : Banerian

It is certified that error appears in the above-identified patent and that said Letters Patent is hereby corrected as shown below:

Column 3, delete lines 3 and 4.

Signed and Sealed this

Ninth Day of February, 1999

Attest:

Attesting Officer

Acting Commissioner of Patents and Trademarks